(12) United States Patent
Devega

(10) Patent No.: US 7,896,838 B2
(45) Date of Patent: Mar. 1, 2011

(54) ILLUMINATED SYRINGE

(76) Inventor: Laura Devega, Dallas, TX (US)

( * ) Notice: Subject to any disclaimer, the term of this patent is extended or adjusted under 35 U.S.C. 154(b) by 513 days.

(21) Appl. No.: 12/079,958

(22) Filed: Mar. 31, 2008

(65) Prior Publication Data

US 2009/0247956 A1 Oct. 1, 2009

(51) Int. Cl.
*A61M 5/00* (2006.01)
(52) U.S. Cl. .......................................................... 604/116
(58) Field of Classification Search ................... 604/116, 604/187
See application file for complete search history.

(56) References Cited

U.S. PATENT DOCUMENTS

| | | | |
|---|---|---|---|
| 6,739,744 B2 * | 5/2004 | Williams et al. | 362/552 |
| 2002/0058230 A1 * | 5/2002 | Savin et al. | 433/31 |

* cited by examiner

*Primary Examiner* — Kevin C Sirmons
*Assistant Examiner* — Bradley J Osinsky
(74) *Attorney, Agent, or Firm* — Thrasher Associates

(57) ABSTRACT

The invention is an apparatus comprising of a syringe, a plunger and a circuit for the purpose of activating a light source to illuminate a target area for application of the contents of the syringe in low-light or no-light situations.

1 Claim, 2 Drawing Sheets

ILLUMINATED SYRINGE

TECHNICAL FIELD

The present invention relates to syringe devices.

PROBLEM STATEMENT

Interpretation Considerations

This section describes the technical field in more detail, and discusses problems encountered in the technical field. This section does not describe prior art as defined for purposes of anticipation or obviousness under 35 U.S.C. section 102 or 35 U.S.C. section 103. Thus, nothing stated in the Problem Statement is to be construed as prior art.

Discussion

Health care providers and those who apply liquids via syringes are often faced with the problem of dispensing the liquid in low-light conditions. In the medical profession, this is typically due to a patient requiring medication during the night. Of course, turning on the light in a hospital room can disturb a resting patient thus hampering recovery. Conversely, without sufficient light, a hypodermic needle may be employed clumsily—whether the application is to a patch of the patient's skin, or into an existing intravenous tube. Indeed, the dispersing person may not be able to tell if the patient/child/animal actually received the liquid. Similar problems occur with the use of the syringes with respect to other industries and uses. The present invention solves these problems.

BRIEF DESCRIPTION OF THE DRAWINGS

Various aspects of the invention, as well as at least one embodiment, are better understood by reference to the following EXEMPLARY EMBODIMENT OF A BEST MODE. To better understand the invention, the EXEMPLARY EMBODIMENT OF A BEST MODE should be read in conjunction with the drawings in which.

SELECTED OVERVIEW OF SELECTED EMBODIMENTS

Figure 1A:
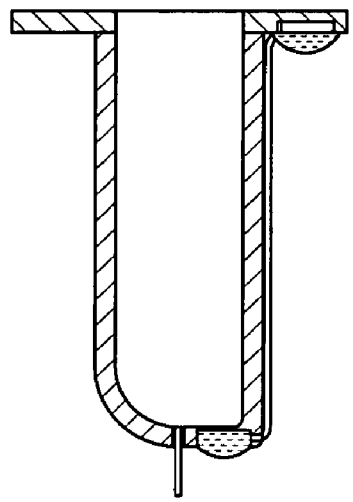
FIG. 1a shows a side-cut view of the invention.

The invention provides technical advantages as a syringe that possesses a self-contained power and light source to illuminate the target area for application of the syringe contents. The invention also possesses the self-contained circuitry to complete the electrical circuit and cause a light, such as an light-emitting diode (LED), to illuminate.

Of course, other features and embodiments of the invention will be apparent to those of ordinary skill in the art. After reading the specification, and the detailed description of the exemplary embodiment, these persons will recognize that similar results can be achieved in not dissimilar ways. Accordingly, the detailed description is provided as an example of the best mode of the invention, and it should be understood that the invention is not limited by the detailed description. Thus, the invention should be read as being limited only by the claims.

AN EXEMPLARY EMBODIMENT OF A BEST MODE

In one exemplary preferred embodiment the invention is applied in a hospital setting at night where a sleeping patient requires medication administered via hypodermic needle — either to a patch of skin, or at the receptor point of an existing intravenous tube. The invention allows for the application of light to the target area from an LED affixed to the syringe.

When reading this section (An Exemplary Embodiment of a Best Mode, which describes an exemplary embodiment of the best mode of the invention, hereinafter "exemplary embodiment"), one should keep in mind several points. First, the following exemplary embodiment is what the inventor believes to be the best mode for practicing the invention at the time this patent was filed. Thus, since one of ordinary skill in the art may recognize from the following exemplary embodiment that substantially equivalent structures or substantially equivalent acts may be used to achieve the same results in exactly the same way, or to achieve the same results in a not dissimilar way, the following exemplary embodiment should not be interpreted as limiting the invention to one embodiment.

Likewise, individual aspects (sometimes called species) of the invention are provided as examples, and, accordingly, one of ordinary skill in the art may recognize from a following exemplary structure (or a following exemplary act) that a substantially equivalent structure or substantially equivalent act may be used to either achieve the same results in substantially the same way, or to achieve the same results in a not dissimilar way.

Accordingly, the discussion of a species (or a specific item) invokes the genus (the class of items) to which that species belongs as well as related species in that genus. Likewise, the recitation of a genus invokes the species known in the art. Furthermore, it is recognized that as technology develops, a number of additional alternatives to achieve an aspect of the invention may arise. Such advances are hereby incorporated within their respective genus, and should be recognized as being functionally equivalent or structurally equivalent to the aspect shown or described.

Second, the only essential aspects of the invention are identified by the claims. Thus, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (for example, one recognizes that "tacking" may be done by nailing, stapling, gluing, hot gunning, riveting, etc., and so a use of the word tacking invokes stapling, gluing, etc., and all other modes of that word and similar words, such as "attaching"). Fourth, unless explicitly stated otherwise, conjunctive words (such as "or", "and", "including", or "comprising" for example) should be interpreted in the inclusive, not the exclusive, sense. Fifth, the words "means" and "step" are provided to facilitate the reader's understanding of the invention and do not mean "means" or "step" as defined in .sctn.112, paragraph 6 of 35 U.S.C., unless used as "means for-functioning-" or "step for-functioning-" in the Claims section.

Of course, the foregoing discussions and definitions are provided for clarification purposes and are not limiting. Words and phrases are to be given their ordinary plain meaning unless indicated otherwise.

Discussion of the Figures

Figure 1B:
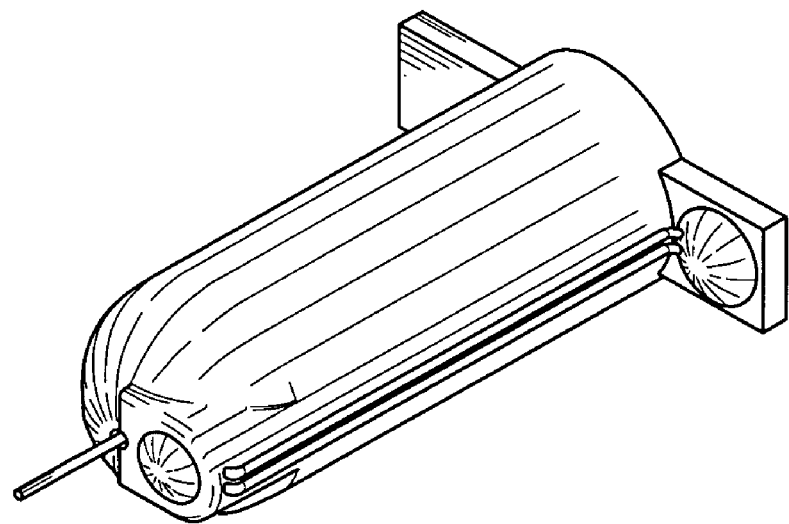
FIG. 1b shows an isometric view of the invention, including a syringe plunger.

The invention is better appreciated by examining the simultaneous figures of FIGS. 1a and 1b. A syringe 100 is generally cylindrical in shape and has an interior cylinder 110, open at a first end 112 that defines an opening, and narrowed to an aperture 130 at a second end, which may be adapted to provide for the attachment of a hypodermic needle 132.

A fluid in the interior chamber of the cylinder 110 is forcibly passable through the aperture 130 at the second end via a plunger 150 which is comprised of a shaft 154, a piston 160 at a first end 152 and a thumb accommodating terminus 170. The outer circumference 162 of the piston 150 is flush with the circumference of the syringe cylinder 110 to effect an air-tight seal of the fluid in the chamber 110. As is appreciated in the art, by applying pressure to the thumb-accommodating terminus 170, fluid may be forced through the aperture 130 of the second end of the syringe 100.

As pressure is applied to the thumb-accommodating terminus 170 the syringe 100 is typically supported by two human fingers, one on each flange 120, 122 at the first end of the syringe 112. This pressure detents the flange 120 and completes a circuit, engaging an electrical source 144 secured in a flange chamber 142. The electrical current travels via a first wire 148 contained in a sleeve 140 that transverses the syringe and couples to a LED 146 in an LED mount 114 of the second end 134. The current then travels through a second wire 149 contained in sleeve 140 that is coupled to the LED 146 and the electrical source 144 in the flange chamber 142.

Figure 2:
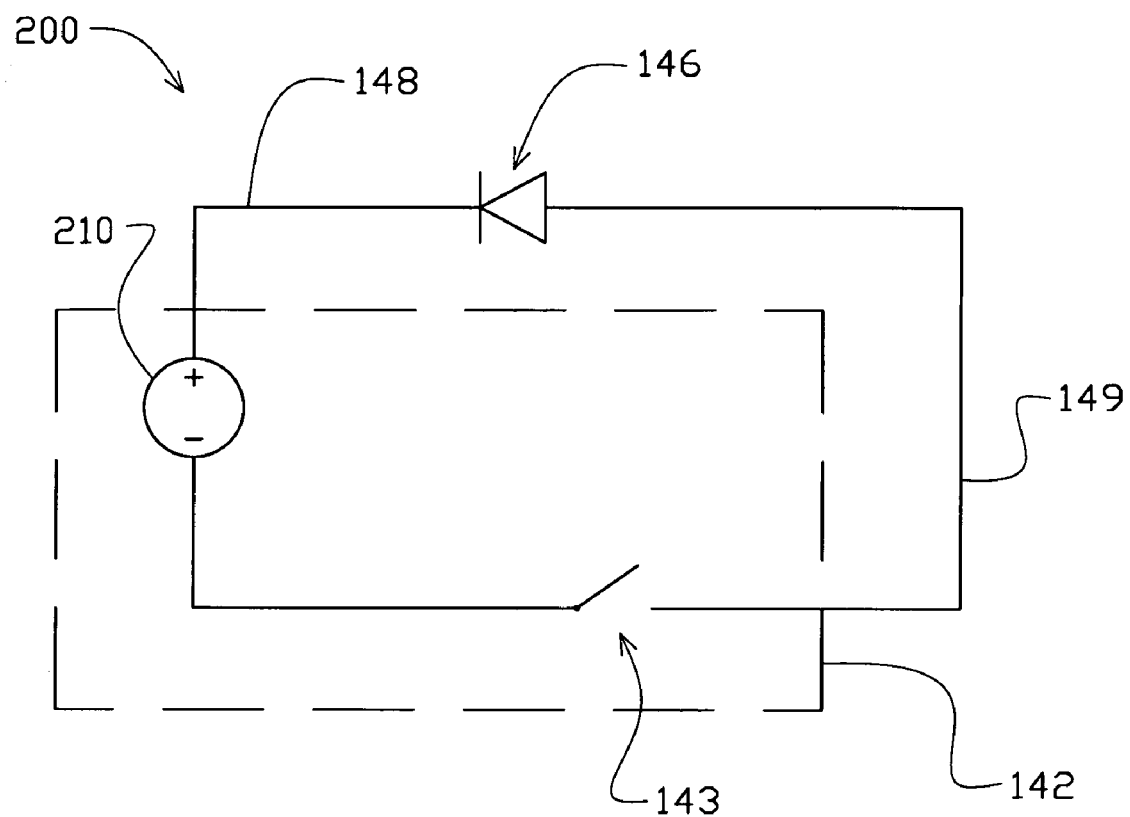
FIG. 2 is a schematic diagram of the invention.

FIG. 2 is a schematic circuit 200 of an embodiment of the invention. The circuit 200 includes a power source 210, which could be a battery or a capacitor, for example, and the power source 210 is preferably secured in the detentable portion/switch 143 of the chamber 142. Accordingly, the detentable portion 143 is illustrated as and effectively performs the function of a switch. The first wire 148 and the second wire 149 are shown as components of the circuit 200 that complete the circuit to the light source 146 illustrated as a diode. The function and alternative structures of the invention are readily apparent to those of skill in the art upon reading the present disclosure.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

I claim:

1. An apparatus, comprising:
    a syringe, comprising
        a generally cylindrical tubing having a first end, a second end, and an inner circumference,
        a first flange located at the first end, the first flange adapted to accommodate a human finger,
        a channel located at the second end,
        a sleeve accommodating a first wire and a second wire, the sleeve transversing the syringe from the first flange to the second end,
        the first flange having a detentable chamber for holding a power source,
        a light emitting diode (LED) mount proximate to the second end, and
        the second end narrowing into a neck so adapted to accommodate the attachment of a hypodermic needle;
    a plunger, comprising
        a shaft having a first end and a second end,
        a piston having an outer circumference flush with the inner circumference of the syringe, the piston coupled to at least the first end of the plunger, and
        a thumb accommodating terminus at the second end of the plunger;
    and
    a circuit, comprising
        the power source secured in the flange chamber,
        an LED affixed to the LED mount,
        the first wire electrically couples the LED to the power source through the sleeve, and
        the second wire extending from the LED through the sleeve and to the cylinder such that the second wire electrically couples the LED to the electric storage means when the chamber is detented.

* * * * *